(12) United States Patent
Gandras et al.

(10) Patent No.: US 9,522,253 B2
(45) Date of Patent: Dec. 20, 2016

(54) DRAINAGE OR FEEDING CATHETER ASSEMBLY

(71) Applicant: Vascular Solutions, Inc., Minneapolis, MN (US)

(72) Inventors: Eric Gandras, Great Neck, NY (US); Howard Root, Minneapolis, MN (US); Dean Peterson, Rogers, MN (US)

(73) Assignees: Vascular Solutions, Inc., Minneapolis, MN (US); Eric Gandras, Great Neck, NY (US)

( * ) Notice: Subject to any disclaimer, the term of this patent is extended or adjusted under 35 U.S.C. 154(b) by 210 days.

(21) Appl. No.: 14/206,940

(22) Filed: Mar. 12, 2014

(65) Prior Publication Data

US 2014/0276628 A1    Sep. 18, 2014

Related U.S. Application Data

(60) Provisional application No. 61/780,832, filed on Mar. 13, 2013.

(51) Int. Cl.
| | |
|---|---|
| *A61M 5/178* | (2006.01) |
| *A61M 25/04* | (2006.01) |
| *A61J 15/00* | (2006.01) |
| *A61M 25/00* | (2006.01) |
| *A61J 1/10* | (2006.01) |

(52) U.S. Cl.
CPC ........... *A61M 25/04* (2013.01); *A61J 15/0046* (2013.01); *A61J 15/0069* (2013.01); *A61J 1/10* (2013.01); *A61M 25/0017* (2013.01); *A61M 2025/0024* (2013.01); *A61M 2025/0063* (2013.01)

(58) Field of Classification Search
CPC ................. A61M 25/0017; A61M 2025/0063; A61M 2025/0024
See application file for complete search history.

(56) References Cited

U.S. PATENT DOCUMENTS

| | | | |
|---|---|---|---|
| 3,996,938 A | 12/1976 | Clark | |
| 5,037,403 A | 8/1991 | Garcia | |
| 5,399,165 A * | 3/1995 | Paul, Jr. ............ | A61M 25/0147 604/174 |
| 6,558,350 B1 | 5/2003 | Hart et al. | |

(Continued)

*Primary Examiner* — Emily Schmidt
(74) *Attorney, Agent, or Firm* — Schwegman Lundberg & Woessner, P.A.

(57) ABSTRACT

Catheter assemblies, kits and methods allowing for the drainage or administration of fluid or small particles are disclosed. A catheter assembly can include a shaft with a lumen, an expandable retention member, an elongate actuation member and a locking mechanism. The expandable retention member can be positioned at a shaft distal end portion and can include one or more filaments forming a plurality of drainage or administration interstices of variable or uniform size. The elongate actuation member can include an actuation member distal end, directly or indirectly engaged with the expandable retention member, and an actuation member proximal end. Movement of the actuation member proximal end relative to a proximal end of the shaft can cause the expandable retention member to change from a lower-profile configuration to a higher-profile configuration. A moved position of the elongate actuation member can be secured by rotating, sliding or otherwise manipulating the locking mechanism.

25 Claims, 10 Drawing Sheets

(56) References Cited

U.S. PATENT DOCUMENTS

| | | | | |
|---|---|---|---|---|
| 6,837,871 B2* | 1/2005 | Gonzales | ............... | A61M 25/04 |
| | | | | 604/104 |
| 7,338,466 B2 | 3/2008 | Hart et al. | | |
| 2005/0033311 A1* | 2/2005 | Guldfeldt | ............... | A61M 25/04 |
| | | | | 606/108 |
| 2010/0331825 A1* | 12/2010 | Hakky | ............... | A61M 25/0017 |
| | | | | 604/544 |
| 2011/0233079 A1* | 9/2011 | Macinnes | ............ | A61B 19/026 |
| | | | | 206/232 |
| 2011/0313403 A1* | 12/2011 | Hruska | ............. | A61M 25/0097 |
| | | | | 604/540 |
| 2012/0078174 A1* | 3/2012 | Tai | ...................... | A61B 17/3415 |
| | | | | 604/96.01 |

\* cited by examiner

DRAINAGE OR FEEDING CATHETER ASSEMBLY

CLAIM OF PRIORITY

This non-provisional patent application claims the benefit of priority under 35 U.S.C. §119(e) to U.S. Provisional Patent Application Ser. No. 61/780,832, entitled "DRAINAGE OR FEEDING CATHETER ASSEMBLY", filed on Mar. 13, 2013, which is hereby incorporated by reference in its entirety.

TECHNICAL FIELD

This patent document pertains to drainage or feeding catheter assemblies and related kits and methods.

BACKGROUND

Catheter assemblies can be inserted into body conduits and body cavities to allow for drainage or administration of fluids, among other things. The ability to place catheter assemblies into a body for the purpose of draining organs or pathologic fluid collections is revolutionizing medical care. Catheter assemblies can obviate the need for more invasive surgical procedures when placed percutaneously. Furthermore, fluids can be administered via a catheter assembly once an access route has been established following assembly placement.

Drainage catheter assemblies can be used to provide an outlet for a body cavity when a normal outlet lumen is compromised, obstructed or unable to be controlled. For example, a drainage catheter assembly can be used to drain urine from a urinary bladder when a urethra is obstructed or when a patient is incapable of controlling his/her urinary system due to sedation or lack of mental capacity. Drainage catheter assemblies can also be used to drain fluid from a kidney or fluid collections in an abdominal abscess.

Feeding catheter assemblies can be used to administer fluids, medications, therapeutic agents or nutrition to a body cavity.

Existing catheter assemblies used for drainage and feeding purposes include either a single distal end lumen or a limited number of discrete side lumens extending through a tubular shaft wall. Retention or anchoring mechanisms used in these catheter assemblies include a balloon-retention design such as the Foley catheter assembly, a loop design with a coaxial locking suture such as the Cope loop or "pigtail" catheter assembly, or a flowered design such as the Malecot tip catheter assembly.

OVERVIEW

The present inventors recognize, among other things, that existing drainage and feeding catheter assemblies can be blocked, particular at a distal end portion of the catheter assemblies, due to debris becoming lodged in one or more discrete drainage or feeding lumens or by blocking the entrance to the lumens. The inventors also recognize that, on occasion, existing drainage and feeding catheter assemblies are used on a semi-permanent basis, but can be inadvertently pulled out of a body cavity due to an inadequate anchoring mechanism.

When these complications occur, catheter assemblies need to be manipulated and either exchanged and replaced, declogged mechanically or chemically, or repositioned. There are instances when dislodgement, for example, cannot be reversed because an access route is no longer available to replace or reposition a catheter assembly through, and a patient may need to undergo a repeat invasive procedure along with the attendant risks of that procedure and the anesthesia required to carry it out. Even worse, premature dislodgement of certain catheter assemblies, such as gastrostomy or cholecystostomy catheter assemblies that can leak acid or bile (respectively) into a peritoneal cavity, can lead to life-threatening complications necessitating emergent surgery. A limitation of existing catheter assemblies is that there is no mechanism to adequately retain them within a linear, straight tract once a body cavity has collapsed and assembly back-out (an occurrence in surgical practice of surgical drains) is desired while still allowing drainage. This is especially important when a fistula to a body organ is present and closure of the fistula needs to occur in a distal-to-proximal direction in order to avoid accumulation of a pathologic fluid collection, such as an abscess.

To help minimize debris blockage, maintain fluid drainage or administration, and resist inadvertent catheter pull out, the present catheter assemblies can include a braided, woven or mesh-like retention member at a distal end where fluids or debris will be encountered. The retention member can allow for removal of fluid or debris while a catheter assembly is indwelling, provide an improved securing mechanism that will allow for retention in linear tracts while still maintaining drainage or administration, and does not rely on balloon technology, which is associated with rupture and or deflation risks. For at least these reasons, the present catheter assemblies can advantageously require less maintenance and provide reduced risks over indwelling time.

The braided, woven or mesh-like retention member can expand outwardly post-insertion such as by pulling on a proximal end of an elongate actuation member (e.g., a suture, a tether, or an elongate tubular structure), which has a distal end operably engaged with the retention member. A position of the elongate actuation member can be locked in place, relative to a catheter shaft, at or near its proximal end using a user-friendly locking mechanism. The locking of the elongate actuation member can secure an expanded orientation of the retention member to prevent inadvertent pull out of the catheter assembly from a body cavity. The retention member advantageously provides a second use as a filter, which can overcome debris blockage problems associated with discrete drainage or feeding lumens, or entrances thereto, of existing catheter assemblies.

To further illustrate the catheter assemblies, kits and methods disclosed herein, a non-limiting list of examples is provided here:

In Example 1, a catheter assembly can comprise a shaft having a lumen, an expandable retention member, an elongate actuation member and a locking mechanism. The shaft can extend from a shaft proximal end portion to a shaft distal end portion. The expandable retention member can be positioned at the shaft distal end portion and can include one or more filaments forming a plurality of drainage or administration interstices. The elongate actuation member can extend from an actuation member proximal end to and actuation member distal end. The actuation member distal end can be directly or indirectly engaged with the expandable retention member, such that movement of the actuation member proximal end relative to a proximal end of the shaft can cause the expandable retention member to change from a lower-profile configuration to a higher-profile configuration or vice-versa. The locking mechanism can be positioned at the shaft proximal end portion and can be configured to move between a first position, in which the elongate actuation member is movable relative to the shaft, and a second position, in which the elongate actuation member is locked relative to the shaft.

In Example 2, the catheter assembly of Example 1 optionally further comprises a distal tip having a lumen positioned at, and coupled to, a distal end portion of the expandable retention member.

In Example 3, the catheter assembly of Example 2 can optionally be configured such that the one or more filaments are integrated into a portion of the distal tip, at the distal end portion of the expandable retention member, and the shaft distal end portion, at a proximal end portion of the expandable retention member.

In Example 4, the catheter assembly of any one or any combination of Examples 2 or 3 can optionally be configured such that the actuation member distal end is coupled to one or both of the distal tip or the expandable retention member, and is thereby operably engaged with the expandable retention member.

In Example 5, the catheter assembly of any one or any combination of Examples 2-4 can optionally be configured such that the lumen of each of the shaft and the distal tip is sized and shaped to receive a guidewire.

In Example 6, the catheter assembly of any one or any combination of Examples 2-5 can optionally be configured such that a maximum outer diameter of the distal tip is less than a maximum outer diameter of the shaft.

In Example 7, the catheter assembly of any one or any combination of Examples 1-6 can optionally be configured such that the one or more filaments form a braided, woven or mesh structure having the plurality of drainage or administration interstices.

In Example 8, the catheter assembly of Example 7 can optionally be configured such that a size of the plurality of drainage or administration interstices is variable and dependent on a diameter or a length of the expandable retention member.

In Example 9, the catheter assembly of any one or any combination of Examples 1-8 can optionally be configured such that the locking mechanism includes a rotary locking mechanism, and the second position of the locking mechanism is rotationally spaced 90 degrees or less from the first position of the locking mechanism.

In Example 10, the catheter assembly of any one or any combination of Examples 1-9 can optionally be configured such that the elongate actuation member includes a grasping member coupled to its proximal end.

In Example 11, the catheter assembly of any one or any combination of Examples 1-10 can optionally further comprise a bifurcated hub, positioned at the shaft proximal end portion, including a first arm, in which the locking mechanism is integrated, and a second arm, configured to attach to a fluid collection or fluid supply reservoir.

In Example 12, the catheter assembly of any one or any combination of Examples 1-11 can optionally be configured such that the shaft includes an unbiased straight configuration from the shaft proximal end portion to the shaft distal end portion.

In Example 13, the catheter assembly of any one or any combination of Examples 1-12 can optionally be configured such that the one or more filaments include a chemical treatment to perform a chemical function on bodily fluid or bodily tissue. The chemical treatment can include a coating of a pharmaceutical agent.

In Example 14, a kit can comprise a guidewire, the catheter assembly of any one or any combination of Examples 1-13, and instructions for using the catheter assembly to allow for drainage or administration of a fluid.

In Example 15, the kit of Example 14 can optionally further comprise one or both of a stylet, configured to be removably insertable into the lumen of the shaft, or an introductory guide sheath, including an opening configured to receive an outer surface of the catheter assembly during insertion. The stylet can facilitate insertion and placement of the catheter assembly into a body cavity, such as by maintaining a low-profile configuration of the expandable retention member.

In Example 16, a method can comprise inserting a catheter assembly, including a shaft having a lumen and a retention member in a lower-profile configuration, through a body conduit and into a portion of a body cavity; expanding the retention member from the lower-profile configuration to a higher-profile configuration, including pulling, in a proximal direction, an elongate actuation member; securing a pulled position of the elongate actuation member, relative to the shaft, through movement of a locking mechanism from a first position to a second position; and draining a fluid from, or administering a fluid to, the body cavity.

In Example 17, the method of Example 16 is optionally configured such that inserting the catheter assembly through the body conduit and into the portion of the body cavity includes guiding the lumen of the shaft over a guidewire until a distal end portion of the shaft is positioned adjacent a juncture of the body conduit and the body cavity.

In Example 18, the method of any one or any combination of Examples 16 or 17 can optionally be configured such that expanding the retention member from the lower-profile configuration to the higher-profile configuration includes increasing a diameter and decreasing a length of the retention member.

In Example 19, the method of any one or any combination of Examples 16-18 can optionally be configured such that expanding the retention member from the lower-profile configuration to the higher-profile configuration includes engaging, in a mating manner, a proximal end portion of the expandable retention member with a juncture of the body conduit and the body cavity.

In Example 20, the method of any one or any combination of Examples 16-19 can optionally be configured such that securing the pulled position of the elongate actuation member includes rotating the locking mechanism 90 degrees or less, from the first position to the second position.

In Example 21, the method of any one or any combination of Examples 16-20 can optionally be configured such that securing the pulled position of the elongate actuation member includes anchoring an implanted position of the catheter assembly, and specifically the retention member, in the body cavity.

In Example 22, the method of any one or any combination of Examples 16-21 can optionally be configured such that securing the pulled position of the elongate actuation member includes maintaining the higher-profile configuration of the retention member in the body cavity for at least 48 hours.

In Example 23, the method of any one or any combination of Examples 16-22 can optionally be configured such that draining the fluid from the body cavity includes filtering fluid through a plurality of interstices formed by one or more interweaved filaments included in the retention member.

In Example 24, the method of any one or any combination of Examples 16-23 can optionally be configured such that administering the fluid into the body cavity includes providing a medication or therapeutic agent into the body cavity.

In Example 25, the method of any one or any combination of Examples 16-24 can optionally further comprise removing the catheter assembly from the body cavity, including moving the locking mechanism from the second position to the first position and pulling on a proximal end portion of the catheter assembly.

In Example 26, the assembly, kit or method of any one or any combination of Examples 1-25 can optionally be configured such that all elements, operations or other options recited are available to use or select from.

These and other examples and features of the present catheter assemblies, kits and methods will be set forth in part in the following Detailed Description. This Overview is intended to provide non-limiting examples of the present subject matter—it is not intended to provide an exclusive or exhaustive explanation. The Detailed Description below is included to provide further information about the present catheter assemblies, kits and methods.

BRIEF DESCRIPTION OF THE DRAWINGS

In the drawings, like numerals can be used to describe similar elements throughout the several views. The drawings illustrate generally, by way of example, but not by way of limitation, various embodiments discussed in the present patent document.

Figure 1:
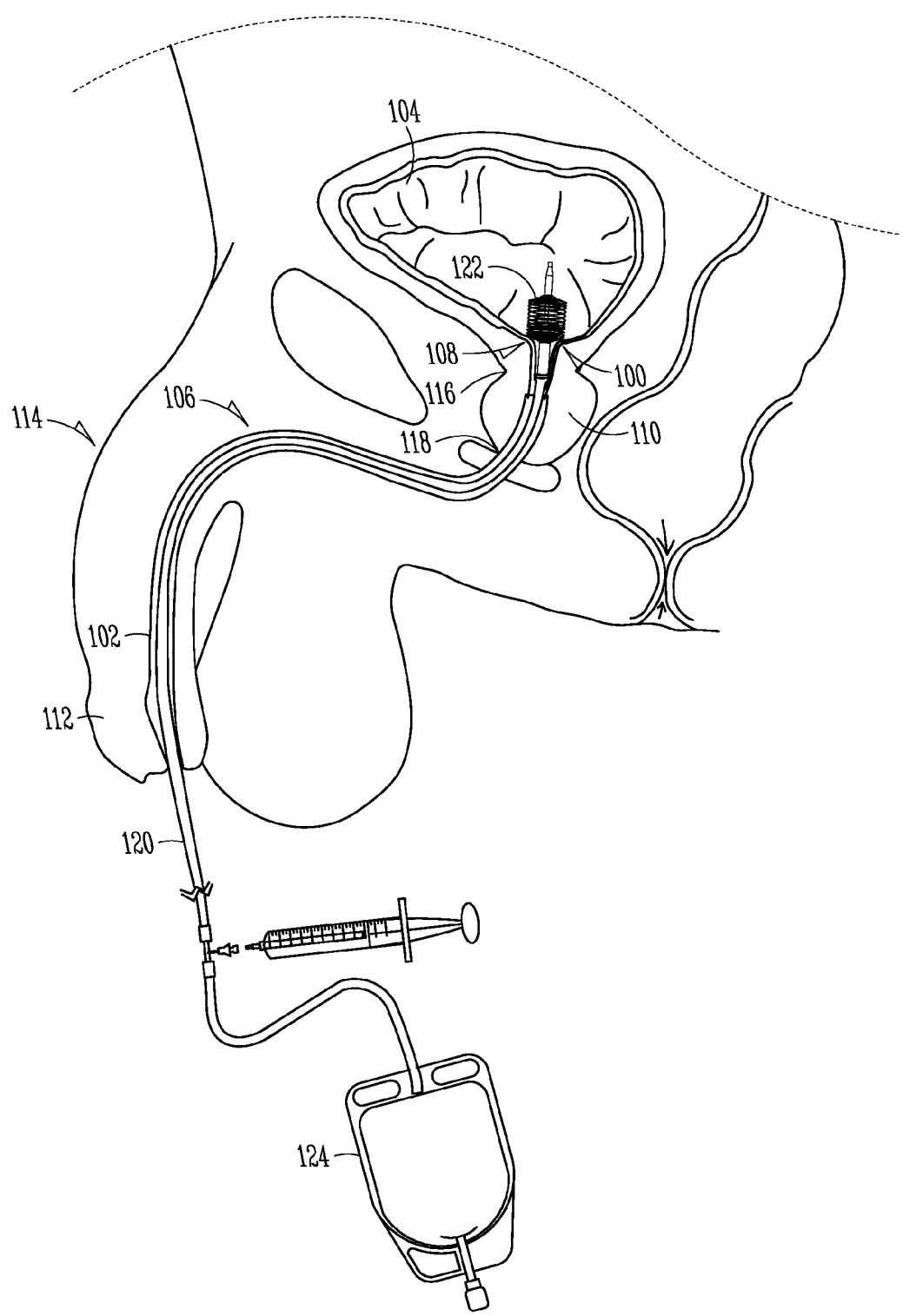
FIG. 1 illustrates portions of a catheter assembly, as constructed in accordance with at least one embodiment, operatively positioned through a urethra conduit and into a bladder cavity of a male patient.

The drawing figures are not necessarily to scale. Certain features and components may be shown exaggerated in scale or in schematic form and some details may not be shown in the interest of clarity and conciseness.

DETAILED DESCRIPTION

The present inventors recognize that it can be desirable to provide a drainage or feeding catheter assembly in which fluid flow is not easily blocked (e.g., due to debris) and that resists inadvertent catheter pull out. The present catheter assemblies can include a distally-located expandable retention member formed from one or more filaments. The one or more filaments can be structured in a braided, woven or mesh-like manner, and can provide a plurality of accessible interstices (e.g., 10-20 interstices, 20-40 interstices, 40-80 interstices, 80-160 interstices or, in some cases, even more) that perform a filter function to overcome debris blockage problems associated with discrete and limited quantity drainage or feeding lumens or entrance ports of existing catheter assemblies. The expandable retention member can, through movement and locking of a proximal end of an elongate actuation member relative to a proximal end of a shaft, assume a relatively high-profile configuration that anchors an implanted position of the catheter assembly and resists inadvertent pull out.

FIG. 1 illustrates portions of a catheter assembly 100 operatively positioned through a urethra conduit 102 and into a bladder cavity 104 of a male patient. In the example shown, the catheter assembly 100 is configured to drain fluid from the bladder cavity 104. In other examples, the catheter assembly 100 can be configured to administer one or more fluids to a body cavity (e.g., the bladder cavity 104) through a body conduit (e.g., the urethra conduit 102).

A urethra 106, including the urethra conduit 102, begins at a bladder neck 108 and passes outwardly through a prostate 110 and a meatus 112 of a penis 114. Sphincters 116, 118 are disposed at opposing ends of the prostate 110. Under normal conditions, the urethra 106 drains urine from the bladder cavity 104 through the control of the sphincters 116, 118, which open and close the urethra 106.

When the urethra 106 is compromised or otherwise blocked, urine cannot naturally drain from the bladder cavity 104, even when the sphincters 116, 118 are open. Under these conditions, it can be desirable to provide a fluid passage from the bladder cavity 104, through the urethra conduit 102, and through the meatus 112 of the penis 114.

The catheter assembly 100 can include a shaft 120 with a lumen and an expandable retention member 122 (or simply, "retention member") disposed at a distal end portion of the shaft 120. The retention member 122 can be configured for movement between a lower-profile configuration (see, e.g., FIG. 10), facilitating insertion through a body conduit (e.g., the urethra conduit 102) and into a body cavity (e.g., the bladder cavity 104), and a higher-profile configuration, facilitating anchoring of the catheter assembly 100 in an operative position as illustrated. A fluid collection reservoir 124 or a fluid applicator can be coupled at a proximal end portion of the shaft 120 such as by way of a hub to gather urine drained from, or inject fluid (e.g., medicine) into, the bladder cavity 104.

Figure 2:
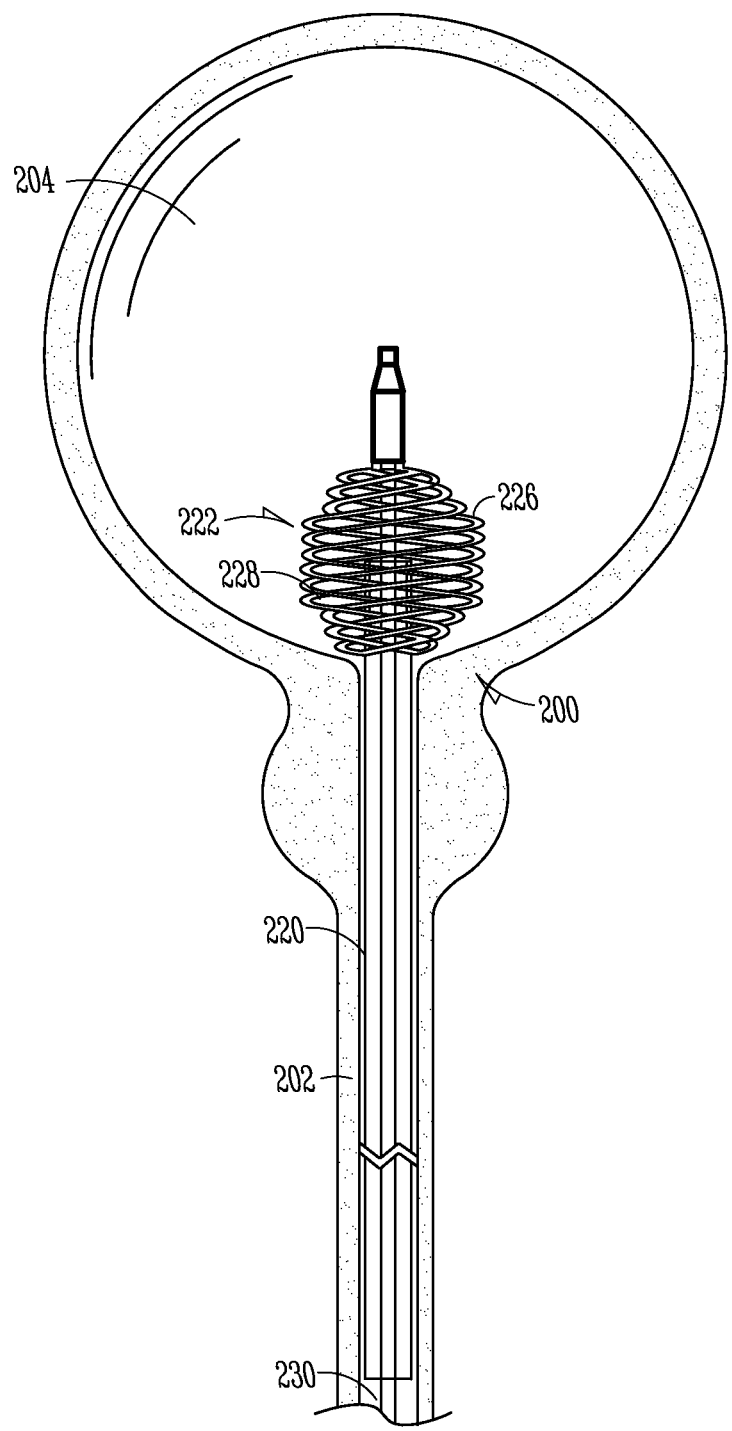
FIG. 2 illustrates an enlarged view of portions of a catheter assembly, as constructed in accordance with at least one embodiment, operatively positioned through a body conduit and into a body cavity.

FIG. 2 illustrates an enlarged view of portions of a catheter assembly 200 operatively positioned through a body conduit 202 and into a body cavity 204.

The prevent inventors recognize that with existing catheter assemblies, including the best Foley catheter assemblies, Cope loop or "pigtail" catheter assemblies, and Malecot tip catheter assemblies, difficulties are often encountered in getting good fluid filling into, or fluid drainage out of, the body cavity 204 due to debris blockage in one or more discrete filling or drainage lumens or blocking the entrance thereto. In addition, these existing catheter assemblies have been found to provide less than adequate resistance to inadvertent pull out from body cavities in a safe and reliable manner.

To help minimize debris blockage and inadvertent catheter pull out, the present catheter assembly 200 can include a braided, woven or mesh-like retention member 222 that can expand outwardly post-insertion, such as by pulling on a proximal end of an elongate actuation member 230, which has a distal end operably engaged with the retention member 222. A position of the elongate actuation member 230 can be easily locked in place, relative to a catheter shaft 220, near its proximal end using a locking mechanism. The locking of the elongate actuation member 230 can lock an expanded, relatively high-profile configuration of the retention member 222 to prevent inadvertent pull out from the body cavity 204. The braided, woven or mesh-like retention member 222 advantageously provides a filter function using a plurality of fluid drainage or fluid administration interstices 228 formed from one or more interweaved filaments 226, for example. The plurality of fluid drainage or fluid administration interstices 228 can overcome debris blockage problems associated with discrete and limited quantity drainage or feeding lumens, such as those included in Cope loop or "pigtail" catheter assemblies, by providing numerous paths for fluid to flow unimpeded into and out of the body cavity 204.

Figure 3:
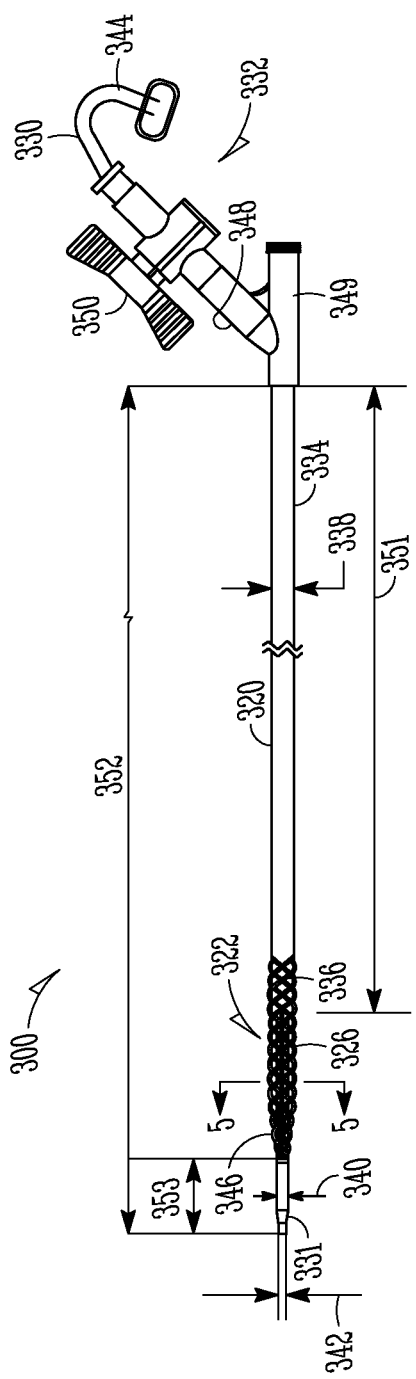
FIG. 3 illustrates a side view of a catheter assembly including an expandable retention member in a relatively low-profile configuration, as constructed in accordance with at least one embodiment.

FIG. 3 illustrates a side view of a catheter assembly 300 including an expandable retention member 322 in a relatively low-profile configuration. The low-profile configuration of the expandable retention member 322 can facilitate insertion of the catheter assembly 300 through a body conduit and into a body cavity. In addition to the expandable retention member 322, the catheter assembly 300 can include a shaft 320 having a lumen, a distal tip 331 having a lumen, a hub 332 and an elongate actuation member 330. The materials used to construct the catheter assembly 300 can be readily sterilized, non-pyrogenic and free of tissue reaction. While various dimensions are disclosed in this document, other dimensions are possible without departing from the scope of the present invention. Construction of the catheter assembly 300 can be determined by its intended use and the size of the associated body conduit and body cavity in which it is to be used.

The shaft 320 can optionally extend a length 351 of 10-50 centimeters (cm), such as about 25 cm, from a shaft proximal end portion 334 to a shaft distal end portion 336. The shaft 320 can be made of a physiological compatible plastic, such as thermoplastic polyurethanes (e.g., 55AE or 55D pellethane) or polyether block amides, and can define an outer surface and an inner surface. The outer surface can include a diameter 338 of 0.065 to 0.5 inches (in), for example, such as about 0.130 in, and the inner surface can include a diameter of 0.037 to 0.450 in, for example, such as about 0.080 in. The opening or lumen path provided by the inner surface can allow advancement of the shaft 320 over a guidewire during insertion of the catheter assembly 300 through a body conduit and into a body cavity. The opening path can also provide housing for intermediate portions of the elongate actuation member 330.

The distal tip 331 can be positioned distal to the shaft distal end portion 336 and can extend a length 353 of 0.5-3 cm, such as about 1 cm. Similar to the shaft 320, the distal tip 331 can be made of a physiological compatible plastic, such as thermoplastic polyurethanes (e.g., 55AE or 55D pellethane) or polyether block amides, and can define an outer surface and an inner surface. The outer surface can optionally include a diameter 340 of 0.05 to 0.4 in, such as about 0.100 in, on a first end and a diameter 342 of 0.03 to 0.1 in, such as about 0.060 in, on a second end. The inner surface can include a diameter of 0.02 to 0.09 in, for example, and can define the opening or lumen path allowing for advancement of the distal tip 331 over a guidewire during insertion of the catheter assembly 300 through a body conduit and into a body cavity. In varying examples, a maximum outer diameter of the distal tip 331 is less than a maximum outer diameter of the shaft 320. From a position distal of the hub 332, portions of the catheter assembly 300 (i.e., the shaft 320, the expandable retention member 322 and the distal tip 331) can optionally extend a length 352 of 15-55 cm, such as about 32-36 cm.

The hub 332 can be positioned at the shaft proximal end portion 334 and can include one or more arm members arranged in a bifurcated Y-shape. A first arm member 348 can include a locking mechanism 350 and a second arm member 349 can be coupled to a fluid collection or fluid supply reservoir. In the example illustrated, the locking mechanism 350 includes a rotary locking mechanism configured to rotate between a first position, in which the elongate actuation member 330 is moveable relative to the shaft 320, and a second position, in which the elongate actuation member 330 is locked relative to the shaft 320. The relative locking between the elongate actuation member 330 and the shaft 320 can secure a relatively high-profile configuration of the expandable retention member 322 to resist inadvertent catheter assembly 300 pull out. In other examples, the locking mechanism 350 can be configured to slide or otherwise move between the first position and the second position.

The elongate actuation member 330 can extend from an actuation member proximal end 344 to an actuation member distal end 346. The actuation member proximal end 344 can be positioned near the locking mechanism 350 and the actuation member distal end 346 can be secured directly or indirectly to the distal tip 331 or the expandable retention member 322, thereby operatively engaging the expandable retention member 322 and the elongate actuation member 330. Intermediate portions of the elongate actuation member 330 can extend through and be housed in the lumen of the shaft 320.

The expandable retention member 322 can be positioned between the distal end portion 336 of the shaft 320 and the distal tip 331. The expandable retention member 322 can be secured to the shaft 320 on a proximal end and the distal tip 331 on a distal end so that the member 322 is not accidently dislodged during use. The expandable retention member 322 can include one or more interweaved filaments 326, which can be integrated into a portion of the shaft 320 and a portion of the distal tip 331 such as by melting component materials and subsequent cooling. The one or more interweaved filaments 326 can include a tubular braid of, for example, a polyether ether ketone (PEEK), polyester, tinned copper, stainless steel or silver material. The filaments 326 can have a diameter of 0.01-0.03 in, such as about 0.014 in.

Figure 4:
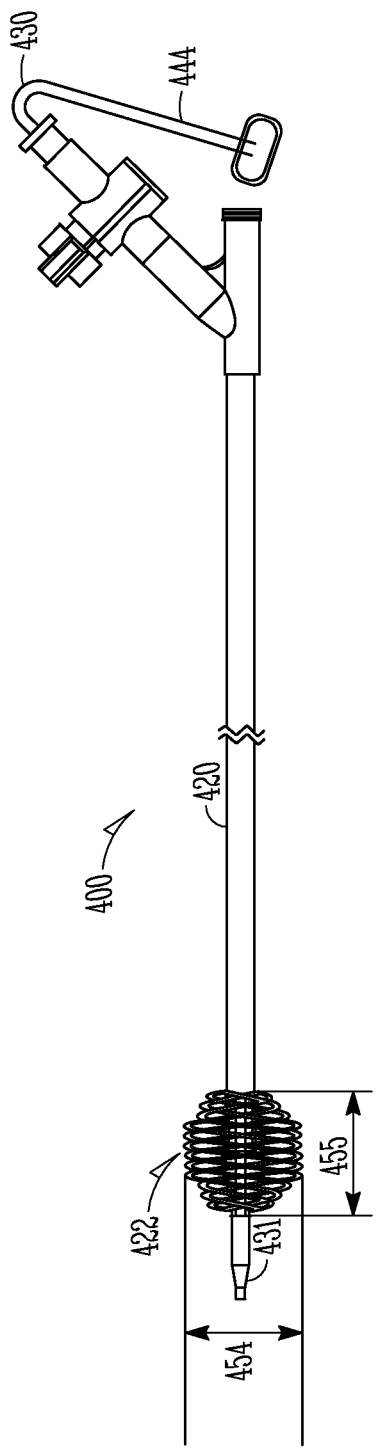
FIG. 4 illustrates a side view of a catheter assembly including an expandable retention member in a relatively high-profile configuration, as constructed in accordance with at least one embodiment.

In operation, the catheter assembly 300 and its expandable retention member 322 can enter through a body conduit and into a body cavity in the lower-profile configuration of FIG. 3 and, when positioned within the body cavity, can be expanded to a higher-profile configuration as illustrated in FIG. 4. The higher-profile configuration of an expandable retention member 422 can be achieved by pulling on or otherwise moving a proximal end 444 of an elongate actuation member 430 relative to a proximal end of a shaft 420.

The pulling of the elongate actuation member 430 can draw a distal tip 431 in a proximal direction causing the expandable retention member 422, which is pressed between the shaft 420 and the distal tip 431, to expand. A diameter 454 of the expandable retention member 422 can be increased and a length 455 of the expandable retention member 422 can be decreased as a result of the pulling action on the elongate actuation member 422. In an example, the length 455 of the expandable retention member 422 is decreased from about 5 cm, in the pre-pulled, lower-profile configuration, to about 2 cm in the post-pulled, higher-profile configuration. In an example, the diameter 454 of the expandable retention member 422 in the higher-profile configuration is about 1.75 cm.

Figure 5:
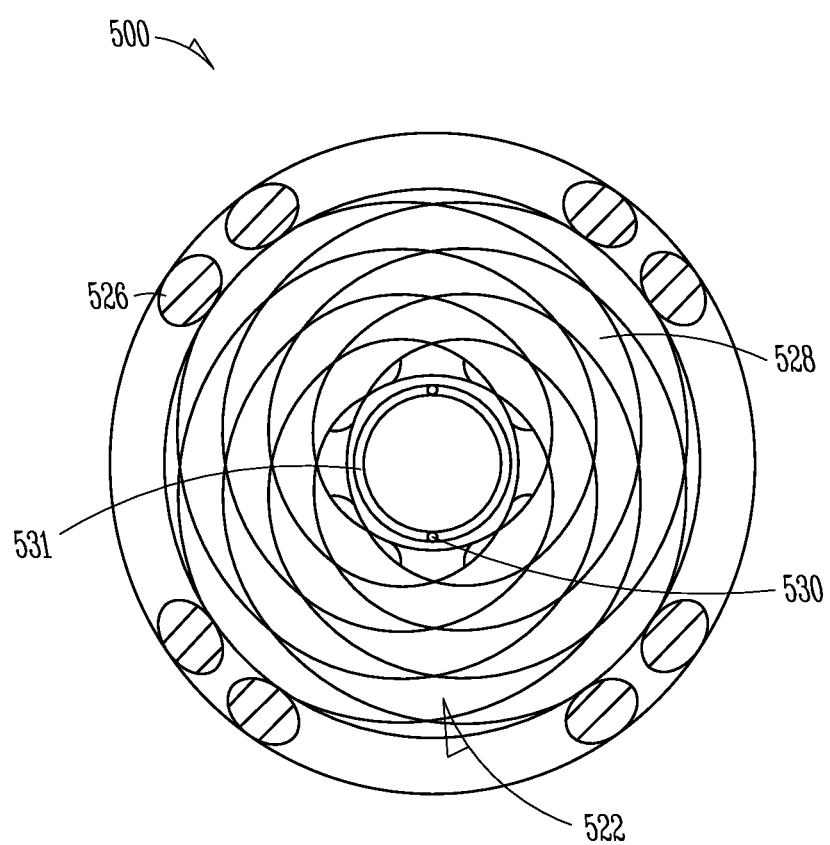
FIG. 5 illustrates a transverse cross-sectional view of a catheter assembly, such as along line 5-5 of FIG. 4, as constructed in accordance with at least one embodiment.

FIG. 5 illustrates a transverse cross-section of portions of a catheter assembly 500, and specifically an expandable retention member 522, a distal tip 531 having a lumen and an elongate actuation member 530, along line 5-5 of FIG. 4. As illustrated in FIG. 5 and further illustrated in the cross-sectional side view of FIG. 8, a distal end of the elongate actuation member 530 can be sandwiched between a portion of the distal tip 531 and one or more interweaved filaments 526 of the expandable retention member 522. This sandwiching can operably engage the elongate actuation member 530, the distal tip 531 and the expandable retention member 522.

In the example illustrated, the expandable retention member 522 can include eight filaments 526 interweaved into a tubular braided structure. A plurality of interstices 528 allowing for unimpeded fluid flow can be formed between the interwoven filaments 526. Optionally, the interwoven filaments 526 can include a chemical treatment configured to perform a chemical function (e.g., reduction or elimination of bacteria) on bodily fluid or bodily tissue.

Figure 6:
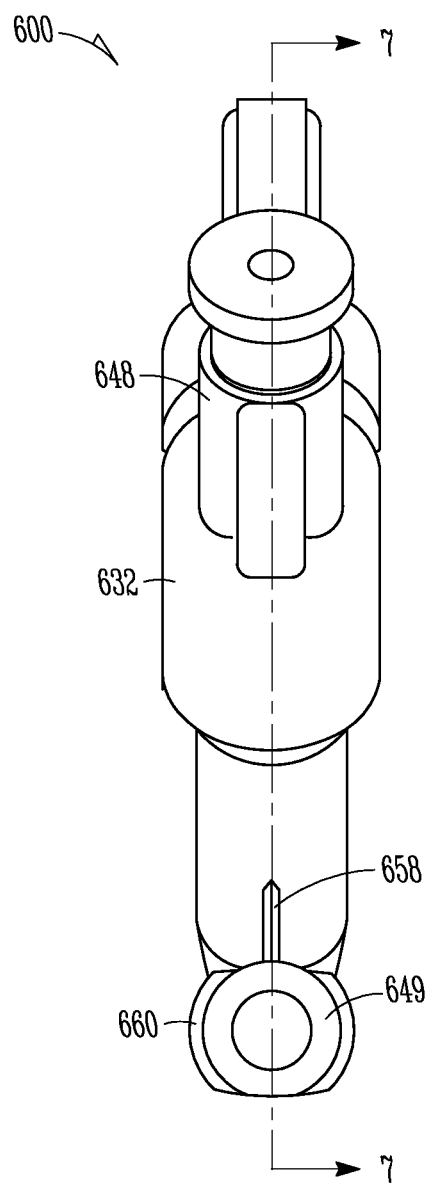
FIG. 6 illustrates a proximal end view of a catheter assembly, as constructed in accordance with at least one embodiment.

FIG. 6 illustrates a proximal end view of a catheter assembly 600. The proximal end of the catheter assembly 600 can include a hub 632 having a first arm member 648 and a second arm member 649. The first arm member 648 can extend at an acute angle relative to the second arm member 649 and can be supported by a rib member 658. The second arm member 649 can extend in alignment with a shaft of the catheter assembly 600 and, on a proximal end, can include one or more threads 660 attachable to a fluid collection or fluid supply reservoir.

Figure 7:
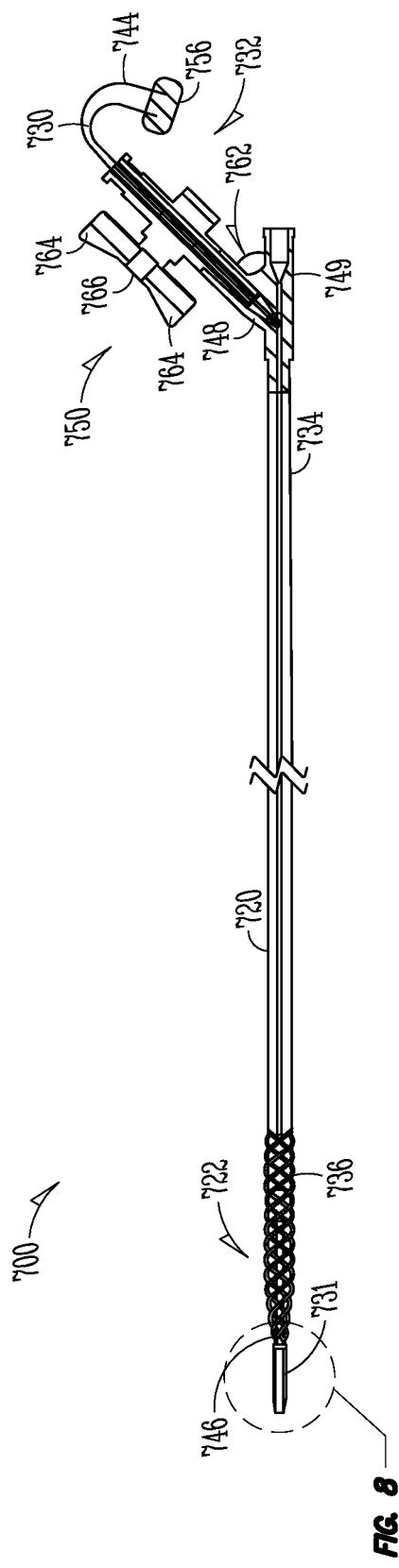
FIG. 7 illustrates a longitudinal cross-sectional view of a catheter assembly, such as along line 7-7 of FIG. 6, as constructed in accordance with at least one embodiment.

FIG. 7 illustrates a longitudinal cross-section of a catheter assembly 700 along line 7-7 of FIG. 6. The catheter assembly 700 can include a shaft 720 having a lumen, a distal tip 731 having a lumen, a hub 732, an elongate actuation member 730 and an expandable retention member 722. The expandable retention member 722 is illustrated in a pre-pulled, lower-profile configuration, which can facilitate insertion of the catheter assembly 700 through a body conduit and into a body cavity.

The shaft 720, the distal tip 731 and an arm member of the hub 732 can each include inner surfaces, which collectively form an opening or lumen path to allow passage of a guidewire, such as during insertion of the catheter assembly 700 through the body conduit and into the body cavity. Portions of the opening path can also provide housing for intermediate portions of the elongate actuation member 730.

The hub 732 can be positioned at a shaft proximal end portion 734. The hub 732 can include one or more arm members arranged in, for example, a bifurcated Y-shape. A first arm member 748 can include a locking mechanism 750 and a second arm member 749 can be coupled to a fluid collection or fluid supply reservoir. The first arm member 748 can extend at an acute angle 762 relative to an extension of the shaft 720.

The elongate actuation member 730 can extend from an actuation member proximal end 744 to an actuation member distal end 746. The actuation member proximal end 744 can be positioned near the locking mechanism 750 and the actuation member distal end 746 can be directly or indirectly secured to the distal tip 731, thereby operatively engaging the expandable retention member 722 and the elongate actuation member 730. Intermediate portions of the elongate actuation member 730 can extend through the lumen of the shaft 720 and into an opening of the hub's first arm member 748. The actuation member proximal end 744 can include a grasping member 756 to facilitate pulling of the elongate actuation member 730 after the expandable retention member 722 is positioned within the body cavity as desired.

The expandable retention member 722 can be positioned between a distal end portion 736 of the shaft 720 and the distal tip 731. The expandable retention member 722 can be secured to the shaft 720, on a proximal end, and the distal tip 731, on a distal end.

The locking mechanism 750 can rotate, slide or otherwise shift between a first position, in which the elongate actuation member 730 is moveable relative to the shaft 720, and a second position, in which the elongate actuation member 730 is locked relative to the shaft 720. In the example illustrated, the locking mechanism 750 includes a pair of rotation force tabs 764 configured to receive a user-initiated force and rotate the locking mechanism 750 from the first position to the second position, or vice-versa. The rotation force tabs 764 can extend in an aligned manner from opposing sides of a central portion 766 of the locking mechanism 750. In the first position, the extension of the rotation force tabs 764 can be aligned with the extension of the hub's first arm member 748. In the second position, the extension of the rotation force tabs 764 can be perpendicular to the extension of the hub's first arm member 748.

In operation, the pulling of the elongate actuation member 730, specifically the grasping member 756, can draw the distal tip 731 in a proximal direction causing the retention member 722, which is pressed between the shaft distal end portion 736 and the distal tip 731, to expand. The expanded orientation of the retention member 722 can be secured by moving the locking mechanism 750 from the first position to the second position, thereby pinching or wrapping an intermediate portion of the elongate actuation member 730 between or around surfaces of the locking mechanism 750 and the hub's first arm member 748.

Figure 8:
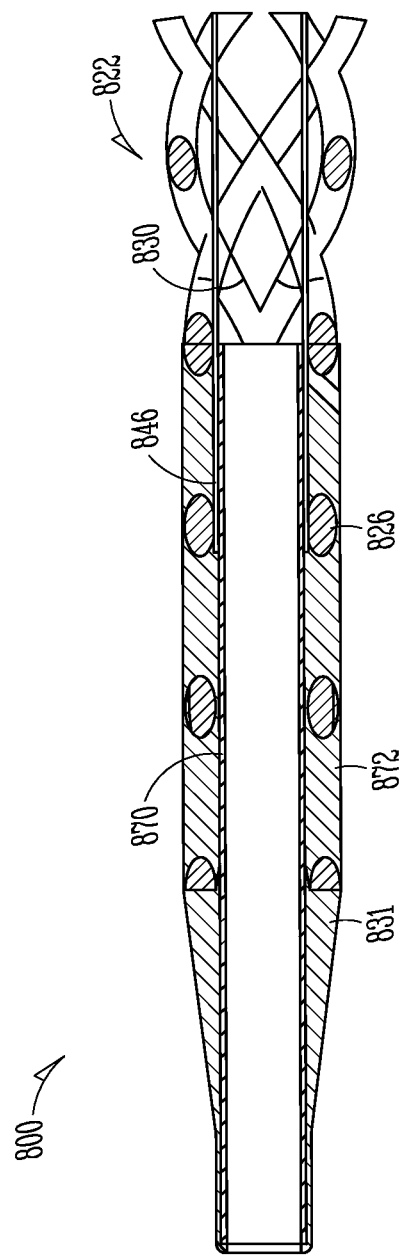
FIG. 8 illustrates a longitudinal cross-section view of distal portions of a catheter assembly, including a distal tip, an expandable retention member and an elongate actuation member, as constructed in accordance with at least one embodiment.

FIG. 8 illustrates a longitudinal cross-section of distal portions of a catheter assembly 800, including a distal tip 831, a distal end 846 of an elongate actuation member 830 and an expandable retention member 822. The fragmented cross-section illustrates that the actuation member distal end 846 can be coupled to one or more interweaved filaments 826 of the expandable retention member 822 and an inner tube 870 of the distal tip 831. This coupling can operably engage the elongate actuation member 830, the distal tip 831 and the expandable retention member 822.

The distal tip 831 can include a generally beveled shape. The beveled shape, which can be provided by an outer tube 872, can facilitate the negotiation of the distal tip 831 through a body conduit and into a body cavity with minimum resistance and difficulty. In particular, the outer tube 872 can deflect during insertion of the catheter assembly 800 and can enable the assembly to follow a path of least resistance, rather than puncturing through an obstruction or tissue wall. As illustrated, the outer tube 872 of the distal tip 831 can be molded around the one or more interweaved filaments 826 of the expandable retention member 822, the latter of which surround portions of the inner tube 870.

A kit can comprise a catheter assembly 100, 200, 300, 400, 500, 600, 700, or 800, a guidewire, and instructions for using the catheter assembly to allow for drainage or administration of a fluid. The guidewire can be advanced through a body conduit and into a body cavity of interest, thereby providing a "railway" to the body cavity. An opening of the catheter assembly, starting with an opening of a distal tip having a lumen, can be passed over an end of the guidewire, and the catheter assembly can be advanced through the body conduit and into the body cavity.

Optionally, the kit can include a stylet, configured to be removably insertable into a lumen of a shaft, or an introductory guide catheter, including an opening configured to receive an outer surface of the catheter assembly during insertion. The stylet and the introductory guide catheter can be used to maintain a relatively low-profile configuration of an expandable retention member during catheter assembly insertion. A stylet, for example, can be provided with a distal end and a proximal end. The distal end can be inserted into a proximal end of the catheter assembly and moved distally along the shaft, where it can contact the distal tip. This contact can fix the distal end of the stylet at the distal tip such that an application of push force to the stylet's proximal end forces the distal tip distally, thereby creating the relatively low-profile configuration of the expandable retention member.

Figure 9:
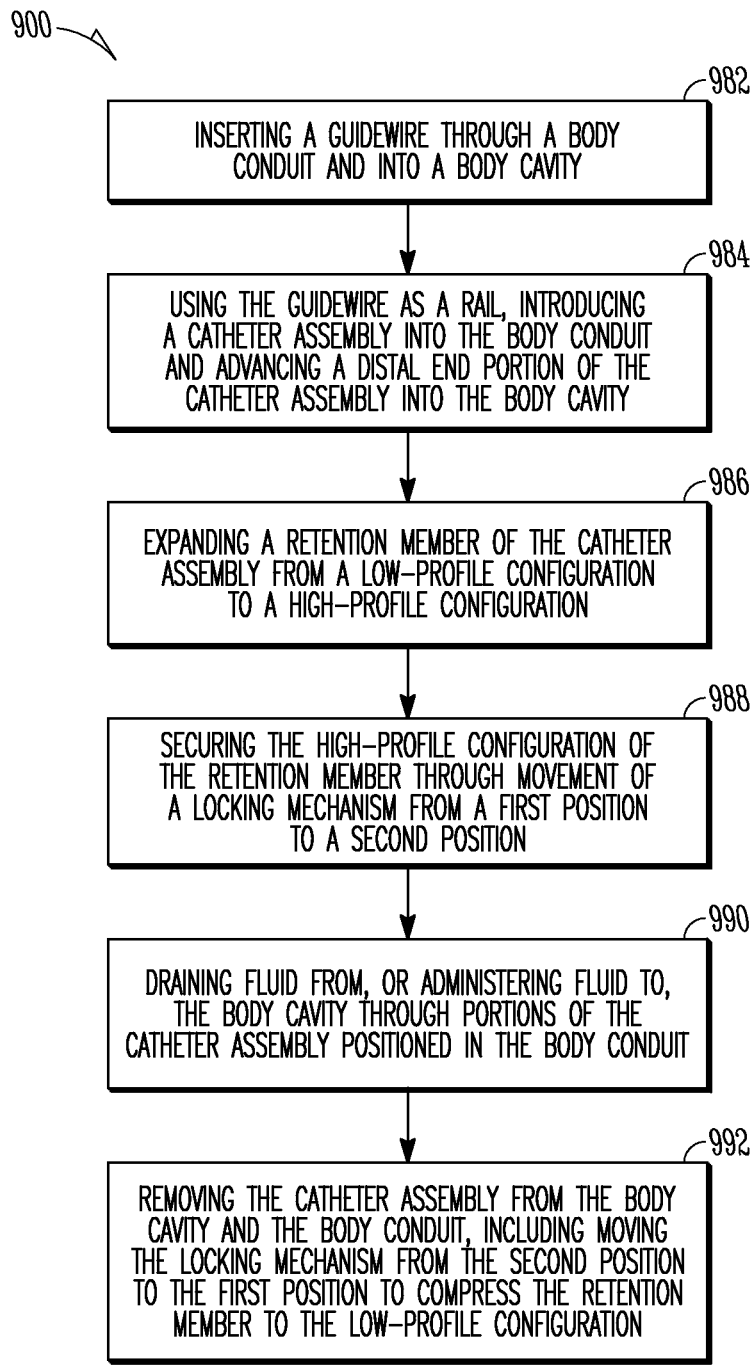
FIG. 9 illustrates an example method of using a catheter assembly, as constructed in accordance with at least one embodiment.

FIG. 9 illustrates an example method 900 of using a catheter assembly as conceived by the present inventors. In operation 982, the catheter assembly, including a shaft and a retention member in a relatively low-profile configuration, can be implanted by first inserting a guidewire through a body conduit and into a body cavity, thereby providing a "railway" to the body cavity. With the guidewire in place, the catheter assembly can be introduced into the body conduit in operation 984, such as by using an over-the-guidewire technique with the guidewire passing through an opening path of the catheter assembly. The catheter assembly can be advanced into the body conduit until a distal end portion of the shaft is positioned adjacent a juncture of the body conduit and the body cavity. A distal tip having a lumen can include a beveled shape that leads the way into the body cavity. Alternatively, the catheter assembly can include a removable needle, allowing the assembly to be implanted as a single integrated unit with the needle being removed post-implant.

The retention member can be expanded from the relatively low-profile configuration to a relatively high-profile configuration in operation 986. The expansion of the retention member can result from pulling on a proximal end of an elongate actuation member, a distal end of which is operatively coupled to the retention member. The pulling of the elongate actuation member can draw the distal tip in a proximal direction causing the retention member, which is pressed between a shaft distal end portion and the distal tip, to increase in diameter and decrease in length. A proximal end portion of the retention member, when in the higher-profile configuration, can include a conical shape to engage in a mating manner with the juncture of the body conduit and the body cavity.

The higher-profile configuration of the retention member can be secured in operation 988 by moving a locking mechanism from a first position to a second position. Movement of the locking mechanism from the first position to the second position can pinch or wrap an intermediate portion of the elongate actuation member between or around surfaces of the locking mechanism. In an example, securing the pulled position of the elongate actuation member includes rotating the locking mechanism 90 degrees or less, from the first position to the second position. The expanded orientation of the retention member, when locked, can adequately anchor an implanted position of the catheter assembly and resist inadvertent pull out, which is particularly advantageous when the catheter assembly is implanted for a semi-permanent use (e.g., a use having duration of 48 hours or more).

In operation 990, a fluid can be drained from, or administered to, the body cavity through the catheter assembly. As fluid is drained through the shaft positioned in the body conduit, a plurality of interstices formed by one or more interweaved filaments included in the retention member can be used to filter the fluid. When fluid is administered to the body cavity, nutrients, medication or therapeutic agents can be communicated from a fluid supply reservoir located outside a patient's body to the internal body cavity.

At the conclusion of fluid drainage or fluid administration, the catheter assembly can be removed from the body cavity and the body conduit in operation 992. To disengage the retention member from the body cavity, the locking mechanism can be moved from the second position to the first position, thereby releasing a position of the elongate actuation member relative to the shaft and allowing the retention member to reassume the lower-profile configuration.

Figure 10:
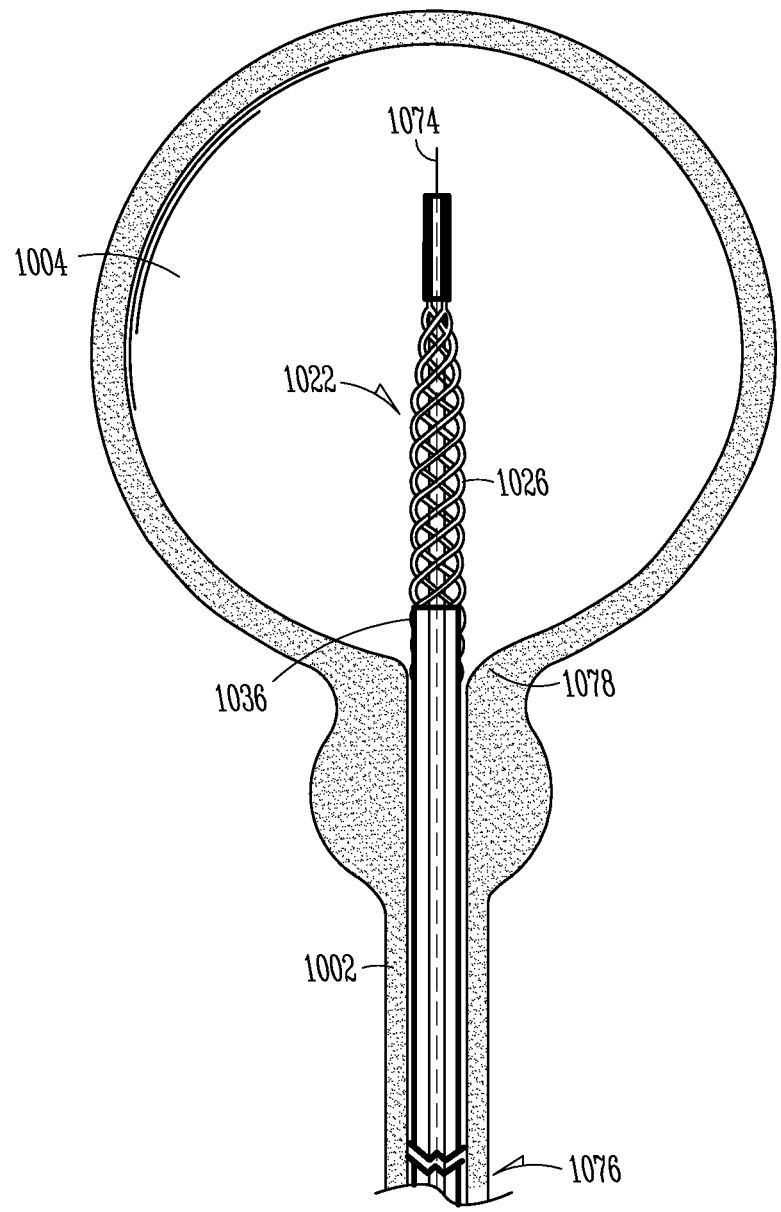
FIG. 10 illustrates an operation included in a method of using a catheter assembly, as constructed in accordance with at least one embodiment.

FIG. 10 illustrates, by way of example, operations 982 and 984 of the method of FIG. 9. A guidewire 1074 can be inserted through a body conduit 1002 and into a body cavity 1004. Having placed the guidewire 1074, a catheter assembly 1000 can be directed over the guidewire 1074 at a proximal end 1076 of the body conduit 1002, advanced through the body conduit 1002, and into the body cavity 1004 with a retention member 1022 in a lower-profile configuration. When in the lower-profile configuration, portions of one or more interweaved filaments 1026 of the retention member 1022 can exhibit a parallel or semi-parallel relationship with an axis of the catheter assembly 1000, and the retention member 1022 can be elongate with a reduced diameter. The lower-profile configuration is particularly appreciated when the catheter assembly 100 is inserted and removed from a patient. Insertion of the catheter assembly 1000 through the body conduit 1002 and into the body cavity 1004 can, in some examples, be facilitated using one or both of a stylet or an introductory guide sheath.

Figure 11:
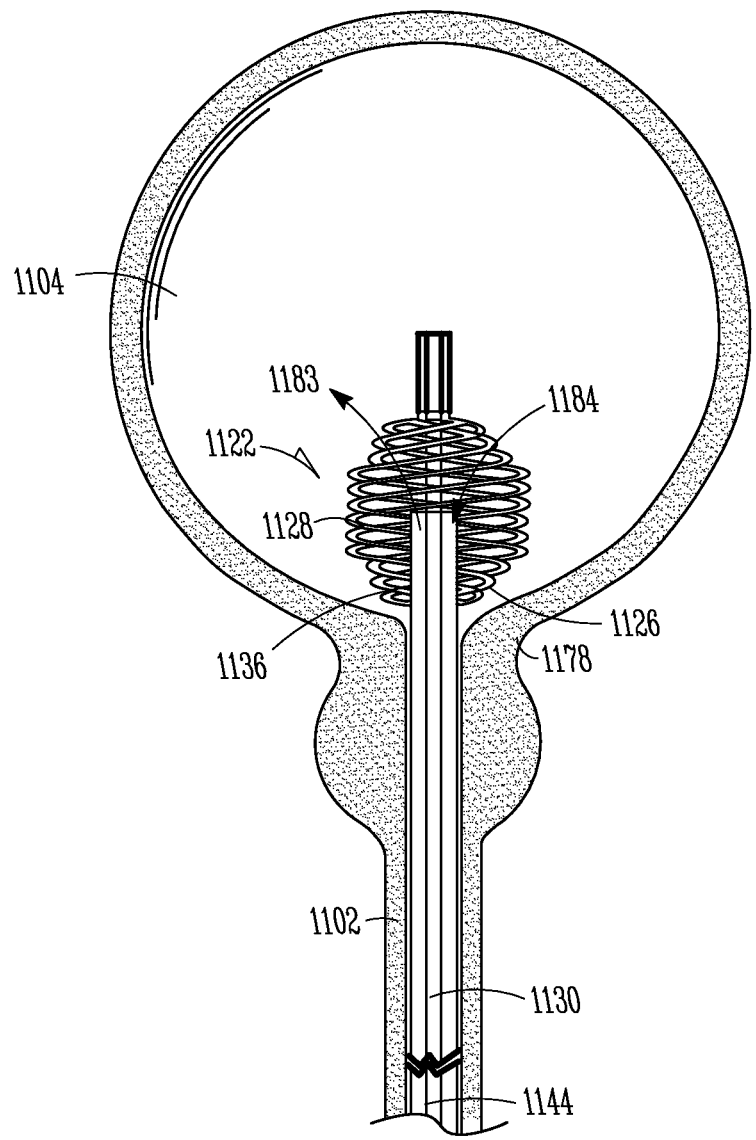
FIG. 11 illustrates an operation included in a method of using a catheter assembly, as constructed in accordance with at least one embodiment.

Once the catheter assembly 1000 is positioned with a shaft distal end 1036 adjacent a juncture 1078 of the body conduit 1002 and the body cavity 1004, the guidewire can be removed. Subsequently, operation 986 of the method of FIG. 9, including the expansion of the retention member 1022 from the lower-profile configuration of FIG. 10 to the higher-profile configuration of FIG. 11, can take place.

The expansion of the retention member 1122 can result from pulling on a proximal end 1144 of an elongate actuation member 1130, a distal end of which is operatively coupled to the retention member 1122. The pulling of the elongate actuation member 1130 can cause an axial contraction and radial expansion of the retention member 1122. Similarly, the interweaved filaments 1126 surrounding a shaft distal end portion 1136 can move generally outward into contact with the juncture 1178 of the body conduit 1102 and the body cavity 1104. The construction of retention member 1122 can provide a high degree of flexibility, which can add significant comfort to the patient, yet provide adequate anchoring within the body cavity 1104 when locked.

In the higher-profile configuration, the retention member 1122 can provide a plurality of interstices 1128 allowing fluid to flow unimpeded into 1183 or out of 1184 the body cavity 1104. Optionally, the shaft distal end 1136 can terminate at the junction 1126, such that the catheter assembly 1100 achieves a low insertion profile. The low insertion profile can ensure that little or no residual quantity of fluid remains in the body cavity 1104 following a drainage procedure, thereby reducing risk of infection to the patient.

Experimental Results:

Laboratory experiments were conducted to help quantify anchoring/retention properties of example catheter assemblies as conceived by the present inventors relative to existing pigtail catheter assemblies. In these experiments, the present catheter assemblies were manufactured to be similar to the assemblies described in association with FIGS. 3 and 4.

1. Experiment 1: In this experiment, a catheter assembly as conceived by the present inventors and a pigtail catheter assembly commercially available from Merit Medical Systems, Inc. of South Jordan, Utah were each inserted through a piece of silicone having a thickness of 0.0658 in using a sharp introducer. After being inserted through the piece of silicone, each catheter assembly was allowed to assume its fully deployed retention configuration. A tensile tester (MI1090) including a 100N load cell was used to measure the amount of force needed to withdraw each catheter assembly in its respective retention configuration from the pierced piece of silicone.

TABLE 1

Experimental results showing that the present catheter assembly exhibits greater retention in a pierced sheet of silicone than a commercially available pigtail catheter assembly.

| Product | Maximum withdrawal force (lbf) |
| --- | --- |
| Merit Medical's pigtail catheter assembly | 2.857 |
| Present catheter assembly | 3.439 |

2. Experiment 2: In this experiment, a catheter assembly as conceived by the present inventors and a pigtail catheter assembly commercially available from Merit Medical Systems, Inc. of South Jordan, Utah were each inserted through a 5.15 mm hole in a piece of silicone having a thickness of 0.0658 in. After being inserted through the hole, each catheter assembly was allowed to assume its fully deployed retention configuration. A tensile tester (MI1090) including a 100N load cell was used to measure the amount of force needed to withdraw each catheter assembly in its respective retention configuration from the 5.15 mm through hole in the piece of silicone.

TABLE 2

Experimental results showing that the present catheter assembly exhibits greater retention in a 5.15 mm hole in a sheet of silicone than a commercially available pigtail catheter assembly.

| Product | Maximum withdrawal force (lbf) |
| --- | --- |
| Merit Medical's pigtail catheter assembly | 1.948 |
| Present catheter assembly | 2.398 |

3. Experiment 3: In this experiment, a catheter assembly as conceived by the present inventors and a pigtail catheter assembly commercially available from Merit Medical Systems, Inc. of South Jordan, Utah were each inserted through an 11.0 mm hole in a piece of silicone having a thickness of 0.0658 in. After being inserted through the hole, each catheter assembly was allowed to assume its fully deployed retention configuration. A tensile tester (MI1090) including a 100N load cell was used to measure the amount of force needed to withdraw each catheter assembly in its respective retention configuration from the 11.0 mm through hole in the piece of silicone.

TABLE 3

Experimental results showing that the present catheter assembly exhibits greater retention in an 11.0 mm hole in a sheet of silicone than a commercially available pigtail catheter assembly.

| Product | Maximum withdrawal force (lbf) |
| --- | --- |
| Merit Medical's pigtail catheter assembly | 1.092 |
| Present catheter assembly | 1.22 |

Closing Notes:

Existing catheter assemblies, including the best Foley catheter assemblies, Cope loop or "pigtail" catheter assemblies, and Malecot tip catheter assemblies, suffer from difficulties in getting good fluid filling into, or fluid drainage out of, a body cavity due to debris blockage in one or more discrete filling or drainage lumens or entrances thereto. In addition, these existing catheter assemblies have been found to provide less than adequate resistance to inadvertent pull out from body cavities in a safe and reliable manner.

To help minimize debris blockage and inadvertent catheter pull out, the present catheter assemblies can include a braided, woven or mesh-like retention member that can expand outwardly post-insertion, such as by pulling on or otherwise moving a proximal end of an elongate actuation member relative to a proximal end of a catheter shaft. The elongate actuation member has a distal end operably engaged with the retention member. A position of the elongate actuation member can be locked in place, relative to the catheter shaft, near its proximal end using a user-friendly locking mechanism. The locking of the elongate actuation member can secure an expanded orientation of the retention member to prevent inadvertent pull out from a body cavity. The braided, woven or mesh-like retention member advantageously provides a filter function that overcomes debris blockage problems associated with discrete drainage or feeding lumens of existing catheter assemblies.

The above Detailed Description includes references to the accompanying drawings, which form a part of the Detailed Description. The Detailed Description should be read with reference to the drawings. The drawings show, by way of illustration, specific embodiments in which the present assemblies, kits and methods can be practiced. These embodiments are also referred to herein as "examples." While certain examples are described with respect to draining fluid from a urinary bladder, it is to be appreciated that the present assemblies, kits and methods are equally applicable to a wide variety of abnormal fluid collections including, without limitation, fluid collections in a kidney, ascites in the abdomen, pleural effusions in the chest and abscesses in a variety of anatomical locations.

The above Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

Certain terms are used throughout this patent document to refer to particular features or components. As one skilled in the art will appreciate, different persons may refer to the same feature or component by different names. This patent document does not intend to distinguish between components or features that differ in name but not in function.

For the following defined terms and numeric values, certain definitions shall be applied, unless a different definition is given elsewhere in this patent document.

The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" refers to a range of numbers that one of skill in the art would consider equivalent to the recited value (e.g., having the same function or result). In many instances, the term "about" can include numbers that are rounded to the nearest significant figure. The recitation of numerical ranges by endpoints includes all numbers and sub-ranges within that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, 3 to 4.25, etc.). The term "patient" is intended to include mammals, such as for human or veterinary applications.

Various beneficial features of the present assemblies, kits and methods are described in context of their relationship in use with a patient's anatomy. For the purposes of providing a clear understanding, the term "proximal" should be understood to mean portions of an assembly or assembly element relatively closer to an operator during use, and the term "distal" should be understood to mean portions of the assembly or assembly element relatively further away from the operator during use.

In the appended claims, the terms "including" and "in which" are used as the plain-English equivalents of the respective terms "comprising" and "wherein." Also, in the following claims, the terms "including" and "comprising" are open-ended, that is, a system, kit, or method that includes features or components in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A catheter assembly, comprising:
    a shaft having a lumen and extending about a longitudinal axis from a shaft proximal end portion to a shaft distal end portion;
    an expandable retention member extending from a retention member proximal end, which is fixedly secured to the shaft distal end portion, to a retention member distal end, the expandable retention member including one or more filaments forming a plurality of drainage or administration interstices;
    an elongate actuation member extending from an actuation member proximal end to an actuation member distal end which is operably engaged with the expandable retention member; and
    a locking mechanism positioned at the shaft proximal end portion and configured to rotate between a first position, in which the elongate actuation member is movable relative to the shaft and the expandable retention member has a lower-profile insertion configuration, and a second position, in which the elongate actuation member is locked relative to the shaft and the expandable retention member has a higher-profile deployed configuration,
    the locking mechanism arranged such that its plane of rotation is non-parallel with the longitudinal axis of the shaft.

2. The catheter assembly of claim 1, further comprising a distal tip having a lumen and fixedly secured to the retention member distal end; and
    wherein proximal movement of the distal tip causes the expandable retention member to assume the higher-profile deployed configuration.

3. The catheter assembly of claim 2, wherein the one or more filaments of the expandable retention member are integrated into a portion of the distal tip at the retention member distal end, and are integrated into the shaft distal end portion at the retention member proximal end.

4. The catheter assembly of claim 2, wherein the actuation member distal end is coupled directly to one or both of the distal tip or the expandable retention member, and is thereby operably engaged with the expandable retention member.

5. The catheter assembly of claim 2, wherein the lumen of each of the shaft and the distal tip is aligned with the longitudinal axis of the shaft and is sized and shaped to receive a guidewire.

6. The catheter assembly of claim 5, further comprising the guidewire, the guidewire positionable within the lumen of each of the shaft and the distal tip.

7. The catheter assembly of claim 2, wherein the distal tip has a length of 0.5 cm to 3 cm, inclusive, and a maximum outer diameter of the distal tip is less than a maximum outer diameter of the shaft.

8. The catheter assembly of claim 2, wherein the distal tip is spaced from the shaft distal end portion such that a portion of the expandable retention member is positioned between the shaft distal end portion and the distal tip.

9. The catheter assembly of claim 1, wherein the one or more filaments of the expandable retention member form a braided, woven or mesh structure having the plurality of drainage or administration interstices.

10. The catheter assembly of claim 1, wherein e elongate actuation member includes a grasping member coupled to its proximal end.

11. The catheter assembly of claim 1, further comprising a bifurcated hub positioned at the shaft proximal end portion and including a first arm, in which the locking mechanism is integrated, and a second arm, configured to attach to a fluid collection or fluid supply reservoir.

12. The catheter assembly of claim 11, wherein rotation of the locking mechanism between the first position and the second position includes rotating the locking mechanism relative to the second arm of the bifurcated hub.

13. The catheter assembly of claim 12, wherein the locking mechanism is configured such that the second position is rotationally spaced 90 degrees or less from the first position.

14. The catheter assembly of claim 1, wherein the shaft includes an unbiased straight configuration from the shaft proximal end portion to the shaft distal end portion.

15. The catheter assembly of claim 1, wherein the one or more filaments include a chemical treatment configured to perform a chemical function on bodily fluid or bodily tissue.

16. A method, comprising:
    inserting a catheter assembly, including a shaft having a lumen, a bifurcated hub positioned at a proximal end of the shaft and having first and second arms, and a retention member in a lower-profile insertion configuration, through a body conduit and into a portion of a body cavity;
    expanding the retention member from the lower-profile insertion configuration to a higher-profile deployed configuration, including pulling, in a proximal direction, an elongate actuation member;
    securing a pulled position of the elongate actuation member relative to the shaft, including rotating a locking mechanism, which is integrated with the first arm of the bifurcated hub, relative to the second arm of the bifurcated hub from a first position to a second position about a plane of rotation that is non-parallel with a longitudinal axis of the shaft; and
    draining a fluid from, or administering a fluid to, the body cavity, including filtering fluid through a plurality of interstices formed by one or more interweaved filaments included in the retention member.

17. The method of claim 16, wherein inserting the catheter assembly through the body conduit and into the portion of the body cavity includes guiding the lumen of the shaft over a guidewire until a distal end portion of the shaft is positioned adjacent a juncture of the body conduit and the body cavity.

18. The method of claim 16, wherein expanding the retention member from the lower-profile insertion configuration to the higher-profile deployed configuration includes increasing a diameter and decreasing a length of the retention member.

19. The method of claim 16, wherein expanding the retention member from the lower-profile insertion configuration to the higher-profile deployed configuration includes engaging a proximal end portion of the expandable retention member with a juncture of the body conduit and the body cavity.

20. The method of claim 16, further comprising removing the catheter assembly from the body cavity, including rotating the locking mechanism from the second position to the first position and pulling on a proximal end portion of the catheter assembly.

21. The method of claim 16, wherein rotating the locking mechanism includes rotating the locking mechanism 90 degrees or less and pinching or wrapping a portion of the elongate actuation member between or around a surface of the locking mechanism.

22. A catheter assembly, comprising:
    a shaft having a lumen and extending about a longitudinal axis from a shaft proximal end portion to a shaft distal end portion;
    an expandable retention member extending from a retention member proximal end, which is fixedly secured to the shaft distal end portion, to a retention member distal end, the expandable retention member including one or more filaments forming a plurality of drainage or administration interstices;
    an elongate actuation member extending from an actuation member proximal end to an actuation member distal end which is operably engaged with the expandable retention member;
    a locking mechanism positioned at the shaft proximal end portion and configured to rotate between a first position, in which the elongate actuation member is movable relative to the shaft and the expandable retention member has a lower-profile insertion configuration, and a second position, in which the elongate actuation member is locked relative to the shaft and the expandable retention member has a higher-profile deployed configuration, about a plane of rotation that is non-parallel with the longitudinal axis of the shaft; and
    a bifurcated hub positioned at the shaft proximal end portion and including a first arm, in which the locking mechanism is integrated, and a second arm, configured to attach to a fluid collection or fluid supply reservoir.

23. The catheter assembly of claim 22, further comprising a distal tip having a lumen and fixedly secured to the retention member distal end; and
    wherein proximal movement of the distal tip causes the expandable retention member to assume the higher-profile deployed configuration.

24. The catheter assembly of claim 23, wherein the lumen of each of the shaft and the distal tip is aligned with the longitudinal axis of the shaft and is sized and shaped to receive a guidewire.

25. The catheter assembly of claim 24, wherein rotation of the locking mechanism between the first position and the second position includes rotating the locking mechanism relative to the second arm of the bifurcated hub.

* * * * *